US012033451B2

(12) United States Patent
Bosua et al.

(10) Patent No.: US 12,033,451 B2
(45) Date of Patent: Jul. 9, 2024

(54) SYSTEMS AND METHODS FOR ANALYTE-BASED ACCESS CONTROLS

(71) Applicant: Know Labs, Inc., Seattle, WA (US)

(72) Inventors: Phillip Bosua, Seattle, WA (US); Ronald Erickson, Seattle, WA (US); Peter Conley, Seattle, WA (US)

(73) Assignee: Know Labs, Inc., Seattle, WA (US)

( * ) Notice: Subject to any disclaimer, the term of this patent is extended or adjusted under 35 U.S.C. 154(b) by 165 days.

(21) Appl. No.: 17/887,923

(22) Filed: Aug. 15, 2022

(65) Prior Publication Data

US 2024/0054839 A1 Feb. 15, 2024

(51) Int. Cl.
*G07C 9/37* (2020.01)
*A61B 5/00* (2006.01)
*G01N 33/497* (2006.01)

(52) U.S. Cl.
CPC .............. *G07C 9/37* (2020.01); *A61B 5/4845* (2013.01); *A61B 5/7275* (2013.01); *G01N 33/4972* (2013.01)

(58) Field of Classification Search
CPC .............................. G01N 33/4972; A61B 5/05
See application file for complete search history.

(56) References Cited

U.S. PATENT DOCUMENTS

| | | | |
|---|---|---|---|
| 4,202,000 A | 5/1980 | Carballes | |
| 6,005,520 A | 12/1999 | Nalbandian et al. | |
| 7,295,827 B2 | 11/2007 | Liu et al. | |
| 8,223,021 B2 | 7/2012 | Goodnow et al. | |
| 8,882,670 B2 | 11/2014 | Hancock | |
| 9,198,607 B2 | 12/2015 | Fischer | |
| 9,864,024 B2 | 1/2018 | Vester | |
| 10,149,629 B2 | 12/2018 | Szczepaniak et al. | |
| 10,258,268 B2 | 4/2019 | Roblyer et al. | |
| 10,405,785 B2 | 9/2019 | Ho et al. | |
| 10,478,101 B1 | 11/2019 | Cespedes et al. | |
| 10,548,503 B2 | 2/2020 | Bosua | |
| 10,617,296 B2 | 4/2020 | Sloan et al. | |
| 10,856,766 B2 | 12/2020 | Leabman | |
| 10,912,500 B2 | 2/2021 | Poeze et al. | |

(Continued)

FOREIGN PATENT DOCUMENTS

| | | |
|---|---|---|
| EP | 3146898 B1 | 11/2018 |
| EP | 3981329 A1 | 4/2022 |

(Continued)

OTHER PUBLICATIONS

Kim, J. et al., "Noninvasive Alcohol Monitoring Using a Wearable Tattoo-Based Iontophoretic-Biosensing System," ACS Sens. 2016, 1, pp. 1011-1019.

(Continued)

*Primary Examiner* — Thomas S McCormack
(74) *Attorney, Agent, or Firm* — Merchant & Gould P.C.

(57) ABSTRACT

One or more analytes are detected non-invasively, and an access level is determined based on the one or more analytes. The one or more analytes indicate at least one of an identity and/or a current status of an individual seeking access, and the access level is based on the identity and/or status of the individual. Access to a location, a device, one or more device functionalities, a vehicle, one or more vehicle functionalities, and the like can be granted based on the access level.

14 Claims, 4 Drawing Sheets

(56) References Cited

U.S. PATENT DOCUMENTS

Figure 1:
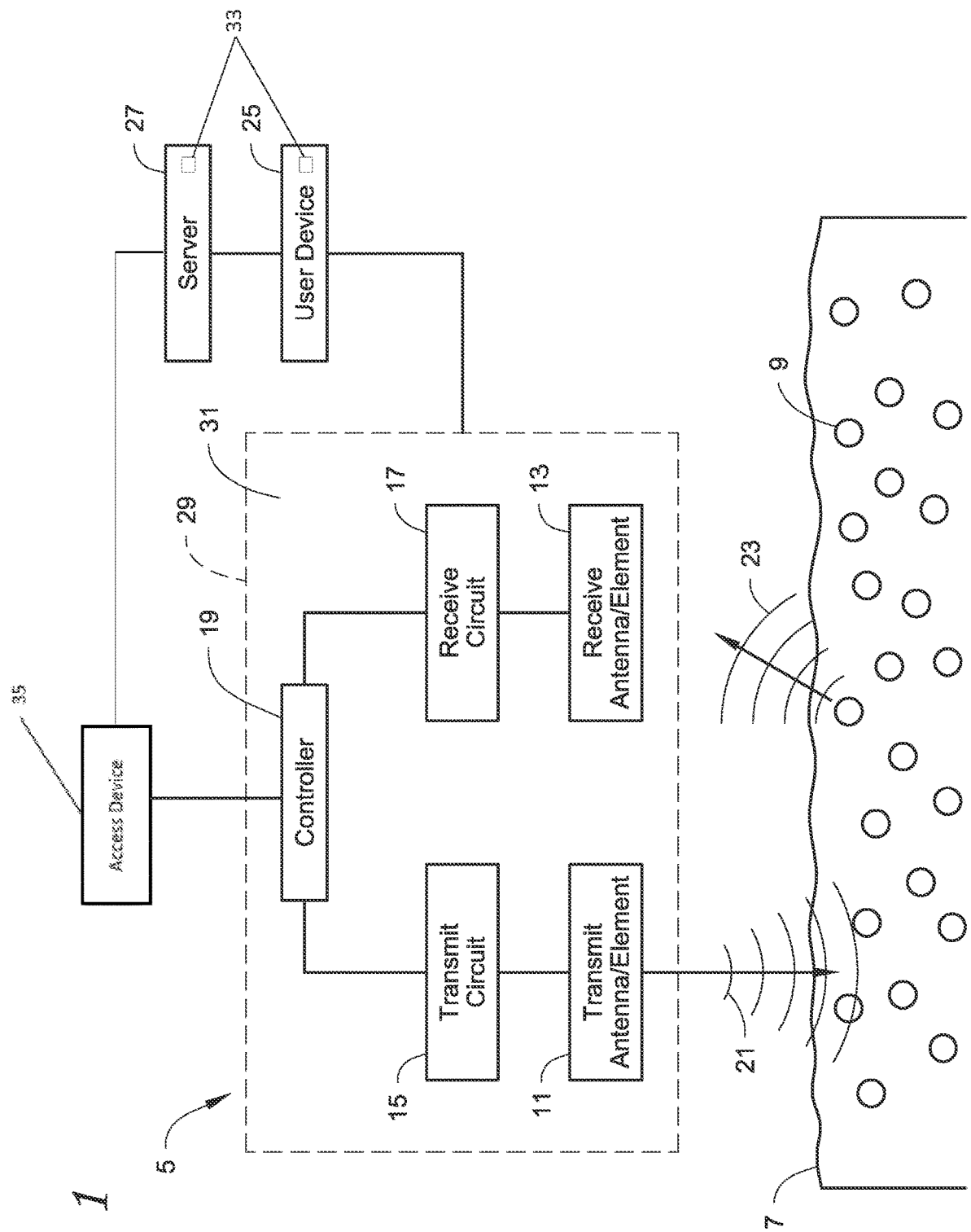

| | | |
|---|---|---|
| 10,932,698 B2 | 3/2021 | Leath et al. |
| 10,956,950 B2 | 3/2021 | Al-Ali et al. |
| 11,031,970 B1 | 6/2021 | Bosua |
| 11,033,208 B1 | 6/2021 | Bosua |
| 11,058,317 B1 | 7/2021 | Bosua |
| 11,058,331 B1 | 7/2021 | Bosua |
| 11,063,373 B1 | 7/2021 | Bosua |
| 11,193,923 B2 | 12/2021 | Bosua |
| 11,202,582 B2 | 12/2021 | Verkruijsse et al. |
| 11,223,383 B2 | 1/2022 | Bosua |
| 11,234,618 B1 | 2/2022 | Bosua et al. |
| 11,234,619 B2 | 2/2022 | Bosua |
| 11,244,753 B2 | 2/2022 | Haggerty et al. |
| 11,284,819 B1 | 3/2022 | Bosua et al. |
| 11,284,820 B1 | 3/2022 | Bosua et al. |
| 11,291,374 B2 | 4/2022 | Lee et al. |
| 11,298,037 B2 | 4/2022 | Leabman |
| 11,330,997 B2 | 5/2022 | Bosua |
| 11,350,830 B2 | 6/2022 | Mckenna et al. |
| 11,360,188 B2 | 6/2022 | Leabman |
| 11,367,525 B2 | 6/2022 | Addison et al. |
| 11,389,093 B2 | 7/2022 | Triman et al. |
| 11,426,104 B2 | 8/2022 | Schurman et al. |
| 2001/0005183 A1 | 6/2001 | Nevermann et al. |
| 2003/0036713 A1 | 2/2003 | Bouton et al. |
| 2004/0065158 A1 | 4/2004 | Schrepfer et al. |
| 2004/0127777 A1 | 7/2004 | Ruchti et al. |
| 2004/0133086 A1 | 7/2004 | Ciurczak et al. |
| 2004/0235536 A1 | 11/2004 | Kim et al. |
| 2009/0213025 A1 | 8/2009 | Coupez et al. |
| 2009/0275814 A1 | 11/2009 | Watanabe et al. |
| 2010/0041969 A1 | 2/2010 | Beise |
| 2011/0028814 A1 | 2/2011 | Petersen et al. |
| 2013/0096396 A1 | 4/2013 | Riedel |
| 2014/0213870 A1 | 7/2014 | Hsu et al. |
| 2016/0051171 A1 | 2/2016 | Pikov et al. |
| 2016/0361002 A1 | 12/2016 | Palikaras et al. |
| 2017/0095667 A1 | 4/2017 | Yakovlev et al. |
| 2017/0181658 A1 | 6/2017 | Dettmann et al. |
| 2018/0028824 A1 | 2/2018 | Pivonka et al. |
| 2018/0132766 A1 | 5/2018 | Lee et al. |
| 2019/0008422 A1 | 1/2019 | Leath et al. |
| 2019/0053741 A1 | 2/2019 | Chaudhry |
| 2019/0104939 A1 | 4/2019 | Costantine et al. |
| 2019/0179008 A1 | 6/2019 | Tavassolian et al. |
| 2019/0269853 A1 | 9/2019 | Doyle et al. |
| 2019/0353752 A1 | 11/2019 | Lin et al. |
| 2019/0357800 A1 | 11/2019 | Bosua |
| 2019/0374135 A1 | 12/2019 | Poeze et al. |
| 2019/0388000 A1 | 12/2019 | Costantine et al. |
| 2020/0054255 A1 | 2/2020 | Conrad et al. |
| 2020/0057163 A1 | 2/2020 | Bromberg |
| 2020/0146584 A1 | 5/2020 | Bosua |
| 2020/0187791 A1 | 6/2020 | Leabman |
| 2020/0187792 A1 | 6/2020 | Leabman |
| 2020/0187793 A1 | 6/2020 | Leabman |
| 2020/0187812 A1 | 6/2020 | Leabman |
| 2020/0187813 A1 | 6/2020 | Leabman |
| 2020/0187814 A1 | 6/2020 | Leabman |
| 2020/0187815 A1 | 6/2020 | Leabman |
| 2020/0187816 A1 | 6/2020 | Leabman |
| 2020/0187817 A1 | 6/2020 | Leabman |
| 2020/0187818 A1 | 6/2020 | Leabman |
| 2020/0187819 A1 | 6/2020 | Leabman |
| 2020/0187820 A1 | 6/2020 | Leabman |
| 2020/0187836 A1 | 6/2020 | Leabman |
| 2020/0187837 A1 | 6/2020 | Leabman |
| 2020/0187867 A1 | 6/2020 | Leabman |
| 2020/0191909 A1 | 6/2020 | Leabman |
| 2020/0191932 A1 | 6/2020 | Leabman |
| 2020/0191933 A1 | 6/2020 | Leabman |
| 2020/0191944 A1 | 6/2020 | Leabman |
| 2020/0191945 A1 | 6/2020 | Leabman |
| 2020/0191947 A1 | 6/2020 | Leabman |
| 2020/0192426 A1 | 6/2020 | Leabman |
| 2020/0192427 A1 | 6/2020 | Leabman |
| 2020/0192428 A1 | 6/2020 | Leabman |
| 2020/0193326 A1 | 6/2020 | Leabman |
| 2020/0195197 A1 | 6/2020 | Leabman |
| 2020/0195293 A1 | 6/2020 | Leabman |
| 2020/0375549 A1 | 12/2020 | Wexler et al. |
| 2021/0059587 A1 | 3/2021 | Feldman et al. |
| 2021/0076988 A1 | 3/2021 | Wang et al. |
| 2021/0186357 A1 | 6/2021 | Bosua et al. |
| 2021/0259571 A1 | 8/2021 | Bosua |
| 2021/0259592 A1 | 8/2021 | Bosua |
| 2021/0259593 A1* | 8/2021 | Bosua ............... A61B 5/14532 |
| 2022/0015695 A1 | 1/2022 | Margarito et al. |
| 2022/0031254 A1 | 2/2022 | Al-Ali et al. |
| 2022/0192494 A1 | 6/2022 | Leabman |
| 2022/0192531 A1 | 6/2022 | Leabman |
| 2022/0248984 A1 | 8/2022 | Poeze et al. |
| 2023/0177905 A1* | 6/2023 | Djoharian ............. G16H 10/60 |
| | | 705/2 |

FOREIGN PATENT DOCUMENTS

| | | |
|---|---|---|
| JP | 2012125382 A | 7/2012 |
| JP | 2014147637 A | 8/2014 |
| KR | 1020160081740 A | 7/2016 |
| WO | 2017163245 A1 | 9/2017 |
| WO | 2019071138 A1 | 4/2019 |
| WO | 2019182638 A1 | 9/2019 |
| WO | 2019198567 A1 | 10/2019 |
| WO | 2019217461 A1 | 11/2019 |
| WO | 2020006077 A1 | 1/2020 |
| WO | 2020037171 A1 | 2/2020 |
| WO | 2021198045 A1 | 10/2021 |
| WO | 2022026623 A1 | 2/2022 |

OTHER PUBLICATIONS

Bravo-Arrabal, J. et al., "Development and Implementation of a Hybrid Wireless Sensor Network of Low Power and Long Range for Urban Environments," Sensors 2021, 21, 567, 27 pages.

Guo, X. et al., "Noninvasive in-vehicle alcohol detection with wavelength-modulated differential photothermal radiometry," Biomedical Optics Express, 2014, vol. 5, No. 7, pp. 2333-2340.

International Search Report and Written Opinion issued for International Patent Application No. PCT/IB2023/058072, Date of mailing: Nov. 13, 2023, 9 pages.

Hanna, J. et al., "Noninvasive, wearable, and tunable electromagnetic multisensing system for continuous glucose monitoring, mimicking vasculature anatomy," Science Advances, 6, eaba5320, 2020 (11 pages).

"Contributes to longer healthy life expectancy with non-invasive vital acquisition sensor," Quantum Operation Co., Ltd., presentation found on Jan. 12, 2021 at https://oi.nttdata.com/program/forum/history/20191118/pdf/03_quantum-op.pdf (14 pages including English translation).

International Search Report and Written Opinion for PCT/US2019/031176, mailed Aug. 23, 2019, 9 pages.

Qiang et al., "Quantitative detection of glucose level based on radiofrequency patch biosensor combined with volume-fixed structures," Biosensors and Bioelectronics 98:357-363, 2017.

Shaker, G. et al., "Non-Invasive Monitoring of Glucose Level Changes Utilizing a mm-Wave Radar System," IJMHCI, vol. 10, Issue 3 (2018): pp. 10-29.

Lien, J. et al., "Soli: Ubiquitous Gesture Sensing with Millimeter Wave Radar," ACM Trans. Graph., vol. 35, No. 4, Article 142, 19 pages (Jul. 2016).

International Search Report and Written Opinion issued for International Patent Application No. PCT/IB2020/062222, Date of mailing: Mar. 25, 2021, 7 pages.

Stojanovic, R. et al., "An optical sensing approach based on light emitting diodes," Journal of Physics: Conference Series 76 (2007), pp. 1-6.

Rossiter, J. et al., "A novel tactile sensor using a matrix of LEDs operating in both photoemitter and photodetector modes," Proc of 4th IEEE International Conference on Sensors (IEEE Sensors 2005), pp. 994-997.

(56) References Cited

OTHER PUBLICATIONS

International Search Report and Written Opinion issued for International Patent Application No. PCT/IB2021/050805, Date of mailing: May 4, 2021, 8 pages.
International Search Report and Written Opinion issued for International Patent Application No. PCT/IB2021/050838, Date of mailing: May 6, 2021, 7 pages.
Mankowska, A. et al., "Association of C-Reactive Protein and Other Markers of Inflammation with Risk of Complications in Diabetic Subjects," The Journal of the International Federation of Clinical Chemistry and Laboratory Medicine, Mar. 2006, 17(1), pp. 8-11.
Mahendran, Y. et al., "Association of Ketone Body Levels With Hyperglycemia and Type 2 Diabetes in 9,398 Finnish Men," Diabetes, Oct. 2013, 62(10), pp. 3618-3626.
Nall, R., "Alcoholic Liver Cirrhosis," Healthline, Updated on Sep. 17, 2018, URL: https://www.healthline.com/health/alcoholic-liver-cirrhosis (Retrieved on May 3, 2021), 4 pages.
Allin, K. et al., "Elevated C-reactive protein in the diagnosis, prognosis, and cause of cancer," Abstract, Crit Rev Clin Lab Sci., Jul.-Aug. 2011, 48(4), 1 page (Retrieved from URL: https://pubmed.ncbi.nlm.nih.gov/22035340/ on May 5, 2021).
"Luteinizing Hormone (LH) Levels Test," MedlinePlus, URL: https://medlineplus.gov/lab-tests/luteinizing-hormone-lh-levels-test/ (Retrieved on May 5, 2021), 6 pages.

* cited by examiner

SYSTEMS AND METHODS FOR ANALYTE-BASED ACCESS CONTROLS

FIELD

This disclosure is directed to access control systems and methods of access control using non-invasive detection of one or more analytes to determine an identity or status of a person seeking access and providing access based on the identity or status.

BACKGROUND

Access to devices, functionalities thereof, locations, and the like can be controlled based on an identity of a user, for example through identification materials such as passes, ID cards, and the like, knowledge-based identification such as passwords, or biometrics such as fingerprints, facial recognition, features of the eye and other such factors. The biometric factors are typically permanent, immutable characteristics of the individual to provide identification but do not reflect a current state of the identified individual.

SUMMARY

This disclosure is directed to access control systems and methods of access control using non-invasive detection of one or more analytes to determine an identity or status of a person seeking access and providing access based on the identity or status.

By using non-invasive detection of analytes to confirm an identity and/or state of an individual seeking access, the granting of access can be made secure and optionally made dependent on a state of the individual, for example, restricting access to the individual when the individual is showing levels of one or more analytes corresponding to intoxication, such as high blood alcohol levels, the presence of opiates or other drugs, and the like.

In an embodiment, an access control system includes a sensor and a controller. The sensor includes an antenna array having at least one transmit antenna and at least one receive antenna. The at least one transmit antenna is positioned and arranged to transmit a transmit signal into a human target, and the at least one receive antenna is positioned and arranged to detect a response resulting from transmission of the transmit signal by the at least one transmit antenna into the human target. The sensor further includes a transmit circuit that is electrically connectable to the at least one transmit antenna. The transmit circuit is configured to generate a transmit signal to be transmitted by the at least one transmit antenna. The transmit signal is in a radio or microwave frequency range of the electromagnetic spectrum. The sensor also includes a receive circuit that is electrically connectable to the at least one receive antenna, the receive circuit configured to receive a response detected by the at least one receive antenna. The controller is configured to determine an identity and/or status of the human target. The determination of identity and/or status is based on a presence or amount of one or more analytes determined by processing of the response. The controller is further configured to provide or deny access to the human target based on the identity and/or status of the individual seeking access.

In an embodiment, the controller is configured to process the response to determine the presence or amount of the one or more analytes. In an embodiment, the controller is configured to provide or deny access to the human target based on the status of the individual seeking access. In an embodiment, the status of the human target includes an intoxication state of the individual seeking access. In an embodiment, the access is access to a location. In an embodiment, the sensor is disposed at an entry to the location. In an embodiment, the sensor is disposed in a mobile device. In an embodiment, the access is access to a device. In an embodiment, the sensor is included in the device. In an embodiment, the access is access to one or more functionalities of a device. In an embodiment, the sensor is included in the device.

In an embodiment, a method of controlling access includes non-invasively detecting one or more analytes. Non-invasively detecting the one or more analytes includes generating a transmit signal using a transmit circuit of a sensor, transmitting the transmit signal into a human target using a transmit antenna of the sensor, the transmit signal in a radio or microwave frequency range of the electromagnetic spectrum, detecting a response resulting from transmitting the transmit signal into the human target using a receive antenna of the sensor, and processing the response to determine a presence or amount of the one or more analytes in the target. The method of controlling access further includes determining, based on the presence or amount of the one or more analytes in the target, an identity and/or status of the human target at a controller and allowing or denying access to the human target based on the identity and/or status of the individual seeking access.

In an embodiment, the controller is configured to provide or deny access to the individual based on the status of the individual seeking access. In an embodiment, the status of the human target includes an intoxication state of the human target. In an embodiment, the access is access to a location. In an embodiment, the access is to a device. In an embodiment, the access is to one or more functionalities of a device.

In an embodiment, a method of access control includes confirming a biological identity of an individual using a non-invasive sensor. The confirming is performed using at least one transmit antenna to transmit first transmit signals in a radio or microwave frequency range of the electromagnetic spectrum into the individual and detecting responses resulting from transmitting the first transmit signals into the individual using at least one receive antenna. The method further includes determining a presence and/or amount of an analyte in the individual using a non-invasive sensor. The determining is performed by transmitting, using at least one transmit antenna, second transmit signals in a radio or microwave frequency range of the electromagnetic spectrum into the individual and detecting responses resulting from transmitting the second transmit signals into the individual using at least one receive antenna. The method also includes permitting or blocking access based on the confirming and the determining.

In an embodiment, the non-invasive sensor used in the confirming is the same non-invasive sensor used in the determining. In an embodiment, the non-invasive sensor used in the confirming is different from the non-invasive sensor used in the determining.

DRAWINGS

Figure 2:
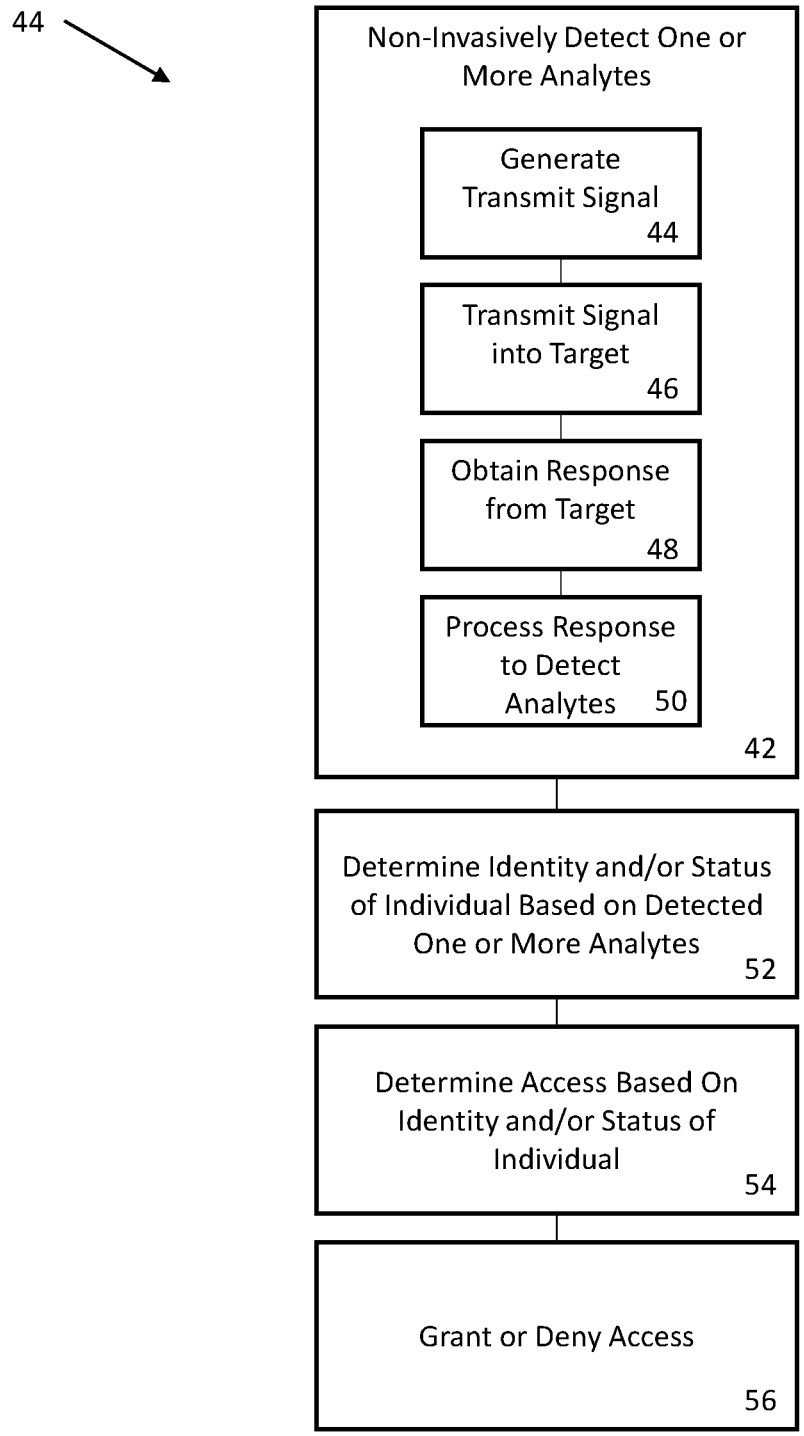
Figure 3:
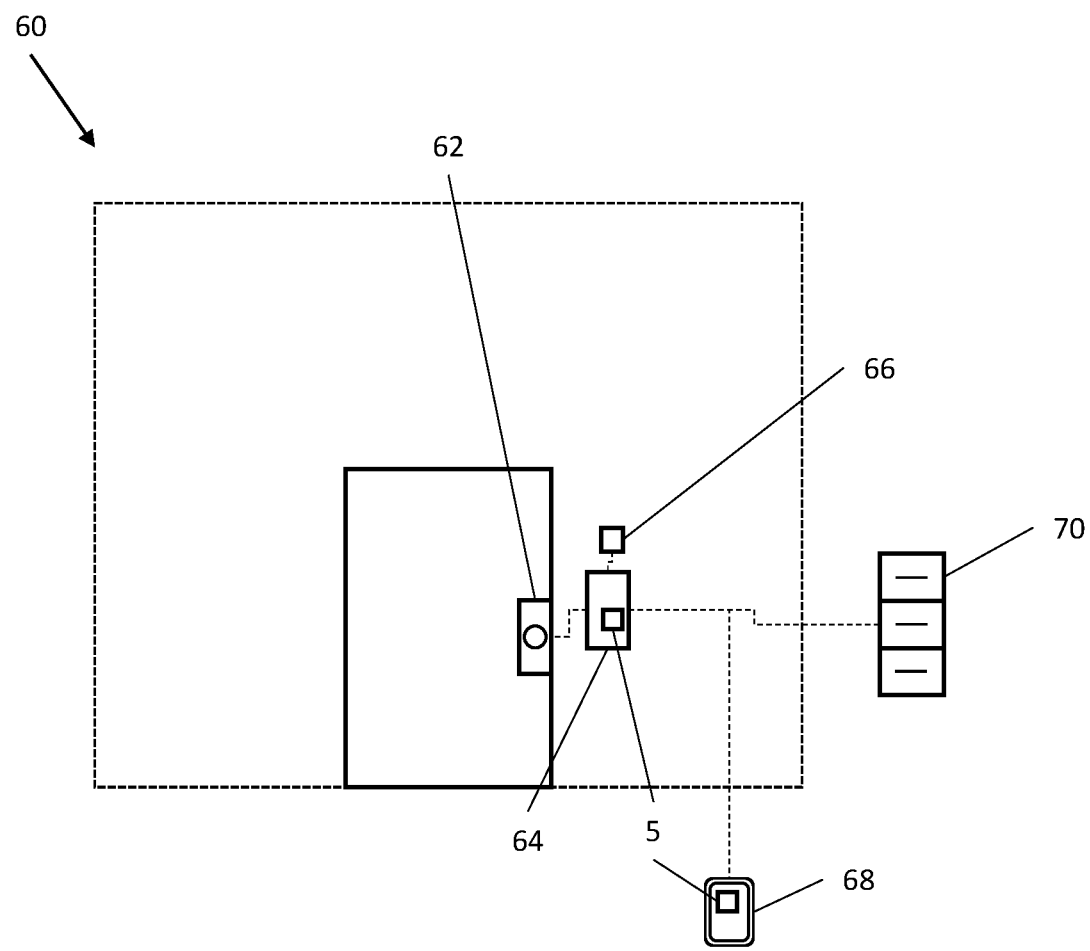

FIG. 1 shows a sensor according to an embodiment.
FIG. 2 shows a flowchart of a method for access control according to an embodiment.
FIG. 3 shows a system for access control for a location according to an embodiment.

Figure 4:
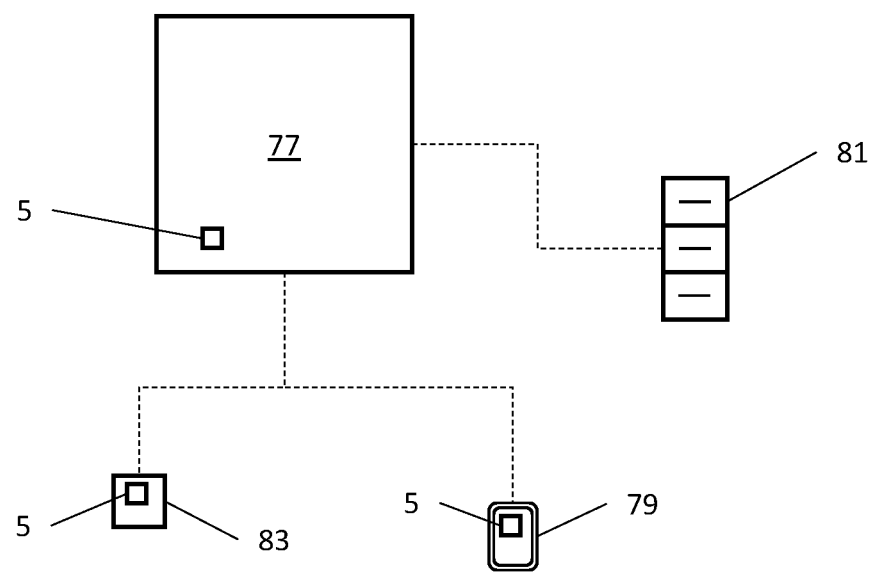

FIG. 4 shows a system for access control for a device according to an embodiment.

DETAILED DESCRIPTION

This disclosure is directed to access control systems and methods of access control using non-invasive detection of one or more analytes to determine an identity or status of a person seeking access and providing access based on the identity or status.

The transmit antenna and the receive antenna are decoupled (which may also be referred to as detuned or the like) from one another. Decoupling refers to intentionally fabricating the configuration and/or arrangement of the transmit antenna and the receive antenna to minimize direct communication between the transmit antenna and the receive antenna, preferably absent shielding. Shielding between the transmit antenna and the receive antenna can be utilized. However, the transmit antenna and the receive antenna are decoupled even without the presence of shielding.

The signal(s) detected by the receive antenna can be analyzed to detect the analyte based on the intensity of the received signal(s) and reductions in intensity at one or more frequencies where the analyte absorbs the transmitted signal. Examples of detecting an analyte using a non-invasive spectroscopy sensor operating in the radio or microwave frequency range of the electromagnetic spectrum are described in WO 2019/217461, U.S. Pat. Nos. 11,063,373, 11,058,331, 11,033,208, 11,284,819, 11,284,820, 10,548,503, 11,234,619, 11,031,970, 11,223,383, 11,058,317, 11,193,923, and 11,234,618, the entire contents of which are incorporated herein by reference.

In one embodiment, the sensor described herein can be used to detect the presence of at least one analyte in a target. In another embodiment, the sensor described herein can detect an amount or a concentration of the at least one analyte in the target. The target can be any target containing at least one analyte of interest that one may wish to detect. The target can be human or non-human, animal or non-animal, biological or non-biological. For example, the target can include, but is not limited to, human tissue, animal tissue, plant tissue, an inanimate object, soil, a fluid, genetic material, or a microbe. Non-limiting examples of targets include, but are not limited to, a fluid, for example blood, interstitial fluid, cerebral spinal fluid, lymph fluid or urine, human tissue, animal tissue, plant tissue, an inanimate object, soil, genetic material, one or more microbes, combinations thereof, and the like.

The analyte(s) can be any analyte that one may wish to detect. The analyte can be human or non-human, animal or non-animal, biological or non-biological. For example, the analyte(s) can include, but is not limited to, one or more of glucose, alcohol, white blood cells, or luteinizing hormone. The analyte(s) can include, but is not limited to, a chemical, a combination of chemicals, a virus, bacteria, or the like. The analyte can be a chemical included in another medium, with non-limiting examples of such media including a fluid containing the at least one analyte, for example blood, interstitial fluid, cerebral spinal fluid, lymph fluid or urine, human tissue, animal tissue, plant tissue, an inanimate object, soil, genetic material, one or more microbes, or combinations thereof. The analyte(s) may also be a non-human, non-biological particle such as a mineral or a contaminant.

The analyte(s) can include, for example, naturally occurring substances, artificial substances, metabolites, and/or reaction products. As non-limiting examples, the at least one analyte can include, but is not limited to, insulin, acarboxyprothrombin; acylcarnitine; adenine phosphoribosyl transferase; adenosine deaminase; albumin; ketones, alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; pro-BNP; BNP; troponin; carnosinase; CD4; ceruloplasmin; chenodeoxycholic acid; chloroquine; cholesterol; cholinesterase; conjugated 1-β hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, analyte-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, *Plasmodium vivax*, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free β-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; analyte-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; lactate; lead; lipoproteins ((a), B/A-1, β); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis, Echinococcus granulosus, Entamoeba histolytica*, enterovirus, *Giardia duodenalisa, Helicobacter pylori*, hepatitis B virus, herpes virus, HIV-1, IgE (atopic disease), influenza virus, *Leishmania donovani*, leptospira, measles/mumps/rubella, *Mycobacterium leprae, Mycoplasma pneumoniae*, Myoglobin, *Onchocerca volvulus*, parainfluenza virus, *Plasmodium falciparum*, polio virus, *Pseudomonas aeruginosa*, respiratory syncytial virus, *rickettsia* (scrub typhus), *Schistosoma mansoni, Toxoplasma gondii, Trepenoma pallidium, Trypanosoma cruzi*/rangeli, vesicular *stomatis* virus, *Wuchereria bancrofti*, yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin.

The analyte(s) can also include one or more chemicals introduced into the target. The analyte(s) can include a marker such as a contrast agent, a radioisotope, or other chemical agent. The analyte(s) can include a fluorocarbon-based synthetic blood. The analyte(s) can include a drug or pharmaceutical composition or metabolites thereof, with non-limiting examples including ethanol or other alcohols; ketones; *cannabis* (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbiturates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The analyte(s) can include other drugs or pharmaceutical compositions. The analyte(s) can include neurochemicals or other chemicals generated within the body, such as, for example, ascorbic acid, uric acid, dopamine, noradrenaline, 3-methoxytyramine (3MT), 3,4-Dihydroxyphenylacetic acid (DOPAC), Homovanillic acid (HVA), 5-Hydroxytryptamine (5HT), and 5-Hydroxyindoleacetic acid (FHIAA).

In an embodiment, the one or more analyte(s) can be detected in some or all of a plurality of tissues, bodily fluids, and the like that are subjected to a transmit signal, in turn resulting in a response signal. For example, a transmit signal into a subject at a location where the transmit signal passes through, for example, skin, bone, muscle, interstitial fluid, blood vessels, and blood can result in a response signal indicative of the presence or amount of analytes present in some or all of the tissues and/or fluids that the transmit signal enters into or passes through. In embodiments, the response signal can be indicative of the presence or amount of some or all of a plurality of organs, such as the liver, the pancreas, the kidneys, the gallbladder, and/or any other such organ. In an embodiment, the response signal can be parsed based on characteristics thereof to estimate or determine the presence or amount of the analyte(s) in particular tissues and/or bodily fluids, for example the presence or amount of the analyte specifically present in blood, interstitial fluid, a particular tissue or organ, or the like.

FIG. 1 shows a sensor at a measurement location according to an embodiment. An embodiment of a non-invasive analyte sensor system with a non-invasive analyte sensor 5 is illustrated. The sensor 5 is depicted relative to a target 7 that contains one or more analyte(s) of interest 9. In this example, the sensor 5 is depicted as including an antenna array that includes a transmit antenna/element 11 (hereinafter "transmit antenna 11") and a receive antenna/element 13 (hereinafter "receive antenna 13"). The sensor 5 further includes a transmit circuit 15, a receive circuit 17, and a controller 19. As discussed further below, the sensor 5 can also include a power supply, such as a battery (not shown in FIG. 1). Sensor 5 can be a non-invasive sensor. Non-invasive sensing can include sensing without disruption to tissue of a subject, for example without requiring injection, implantation into the subject, or the like. It is understood that while sensor 5 is a non-invasive sensor capable of non-invasive sensing, it can also be used to detect the one or more analytes in samples that have been obtained from a subject such as blood or tissue samples.

The analyte(s) of interest 9 are to be detected at target 7. The target can be one or more parts of a person seeking access to the device or location based on detection of the one or more analytes by the sensor 5. For example, the target 7 can be any one or more of, for example, the lower left leg, upper left leg, lower right leg, upper right leg, lower left arm, upper left arm, groin, abdomen, chest, neck, and/or the head of the individual seeking access to the device or location.

The transmit antenna 11 is positioned, arranged and configured to transmit a signal 21 that is the radio frequency (RF) or microwave range of the electromagnetic spectrum into the target 7. The transmit antenna 11 can be an electrode or any other suitable transmitter of electromagnetic signals in the radio frequency (RF) or microwave range. The transmit antenna 11 can have any arrangement and orientation relative to the target 7 that is sufficient to allow the analyte sensing to take place. In one non-limiting embodiment, the transmit antenna 11 can be arranged to face in a direction that is substantially toward the target 7.

The signal 21 transmitted by the transmit antenna 11 is generated by the transmit circuit 15 which is electrically connectable to the transmit antenna 11. The transmit circuit 15 can have any configuration that is suitable to generate a transmit signal to be transmitted by the transmit antenna 11. Transmit circuits for generating transmit signals in the RF or microwave frequency range are well known in the art. In one embodiment, the transmit circuit 15 can include, for example, a connection to a power source, a frequency generator, and optionally filters, amplifiers or any other suitable elements for a circuit generating an RF or microwave frequency electromagnetic signal. In an embodiment, the signal generated by the transmit circuit 15 includes a frequency in the range from about 10 kHz to about 100 GHz. In another embodiment, the frequency can be in a range from about 300 MHz to about 6000 MHz. In an embodiment, the transmit circuit 15 can be configured to sweep through a range of frequencies that are within the range of about 10 kHz to about 100 GHz, or in another embodiment a range of about 300 MHz to about 6000 MHz.

The receive antenna 13 is positioned, arranged, and configured to detect one or more electromagnetic response signals 23 that result from the transmission of the transmit signal 21 by the transmit antenna 11 into the target 7 and impinging on the analyte(s) 9. The receive antenna 13 can be an electrode or any other suitable receiver of electromagnetic signals in the radio frequency (RF) or microwave range. In an embodiment, the receive antenna 13 is configured to detect electromagnetic signals including a frequency in the range from about 10 kHz to about 100 GHz, or in another embodiment a range of about 300 MHz to about 6000 MHz. The receive antenna 13 can have any arrangement and orientation relative to the target 7 that is sufficient to allow detection of the response signal(s) 23 to allow the analyte sensing to take place. In one non-limiting embodiment, the receive antenna 13 can be arranged to face in a direction that is substantially toward the target 7. When the target 7 is a living subject or a part thereof, the signal obtained by receive antenna 13 can be indicative of the analyte(s) present in at least both the blood and the interstitial fluid of the living subject.

The receive circuit 17 is electrically connectable to the receive antenna 13 and conveys the received response from the receive antenna 13 to the controller 19. The receive circuit 17 can have any configuration that is suitable for interfacing with the receive antenna 13 to convert the electromagnetic energy detected by the receive antenna 13 into one or more signals reflective of the response signal(s) 23. The construction of receive circuits are well known in the art. The receive circuit 17 can be configured to condition the signal(s) prior to providing the signal(s) to the controller 19, for example through amplifying the signal(s), filtering the signal(s), or the like. Accordingly, the receive circuit 17 may include filters, amplifiers, or any other suitable components for conditioning the signal(s) provided to the controller 19.

The controller 19 controls the operation of the sensor 5. The controller 19, for example, can direct the transmit circuit 15 to generate a transmit signal to be transmitted by the transmit antenna 11. The controller 19 further receives signals from the receive circuit 17. The controller 19 can optionally process the signals from the receive circuit 17 to detect the analyte(s) 9 in the target 7. In one embodiment, the controller 19 may optionally be in communication with at least one external device 25 such as a user device and/or a remote server 27, for example through one or more wireless connections such as Bluetooth, wireless data connections such a 4G, 5G, LTE or the like, or Wi-Fi. If provided, the external device 25 and/or remote server 27 may process (or further process) the signals that the controller 19 receives from the receive circuit 17, for example to detect the analyte(s) 9. If provided, the external device 25 may be used to provide communication between the sensor 5 and the remote server 27, for example using a wired data connection or via a wireless data connection or Wi-Fi of the external device 25 to provide the connection to the remote server 27. In an embodiment, the external device 25 is a device to which access is controlled based on the one or more analytes detected by the sensor 5. In an embodiment, the external device 25 is an access control to a location, such as a gate, door, elevator, or controls thereof, and the like. In an embodiment, the external device is a mobile device of the individual seeking access controlled based on the one or more analytes detected by the sensor 5.

In an embodiment, controller 19 can be configured to determine a presence or amount of the one or more analytes at the target based on the return signal. In an embodiment, the external device 25 or remote server 27 can include a controller 33 configured to determine the presence or amount of the one or more analytes at the target based on the return signal. At least one of controllers 19 or 33 is configured to determine an identity and/or a status of the individual including the target 7 based on the presence or amount of the one or more analytes. The determination of identity and/or status can be based by comparing the presence or amount of the one or more analytes to values for the one or more analytes that are associate with or indicative of the identity and/or the status of the individual. Identity can be a specific identity of an individual, confirmation that the individual is part of a particular group, or the like. Status can be a current state of the individual such as an intoxication status based on the presence or amount of one or more intoxicants such as alcohol, prescription or recreational drugs, or the like. Other example statuses can include tiredness or exhaustion, attentiveness, sickness, and the like. These statuses can be based on the presence or amounts of least some of the one or more analytes such as biomarkers associated with the statuses, drugs or associated compounds having the statuses as a side effect or resulting condition, particular pathogens or indicators thereof, and the like. Based on the particular identity and/or status, at least one of the controllers 19 and/or 33 can determine an access permission for the individual including target 7. The access permission is determined based on the identity and/or status of the individual. The access permission can be based at least in part on the identity of the individual, such as being an owner of a device or the location, being a person authorized to enter a location or access a device or functionalities thereof, being part of a set of people granted access to a location, or the like. The access permission can be based at least in part on the status of the individual, such as not being intoxicated by alcohol and/or other drugs, in a state of sufficient alertness, not carrying communicable diseases, or the like. In embodiments, both the identity and the status can be used to determine the access permission, such as only allowing access to specific persons, and doing so conditionally based on the status. In embodiments, additional external factors can be included in the determination of the access permission, such as date, time, triggers such as events, and the like. For example, access to a location can be restricted to certain dates and/or ranges of hours in addition to the identity and/or the status of the individual seeking access. The controller 19 and/or 33 can communicate with an access device 35 to provide or prevent access based on the determined access control. In an embodiment, the access device 35 can be, for example, a lock for a gate or door, a door and/or travel controls for an elevator, or any other suitable device for granting or preventing access to a location or device to the individual. In embodiments, the access permission can relate to complete access to a location or a device. In an embodiment, the access permission relates to specific functionalities of a device such as access to particular applications such as software applications, access to one or more subsets of functionalities of the device, and the like. For example, access permissions for a mobile device can include requiring confirmation of identity and/or status of the user to allow financial transactions to be made, limits on contacts that can be messaged based on identity and/or status of the user, and the like. Particular functionalities of other devices such as industrial or construction equipment and the like can likewise be controlled based on identity and/or status of the user, for example, allowing access to different functionalities for different sets or classifications of individuals and/or the particular statuses thereof.

With continued reference to FIG. 1, the sensor 5 may include a sensor housing 29 (shown in dashed lines) that defines an interior space 31. Components of the sensor 5 may be attached to and/or disposed within the housing 29. For example, the transmit antenna 11 and the receive antenna 13 are attached to the housing 29. In some embodiments, the antennas 11, 13 may be entirely or partially within the interior space 31 of the housing 29. In some embodiments, the antennas 11, 13 may be attached to the housing 29 but at least partially or fully located outside the interior space 31. In some embodiments, the transmit circuit 15, the receive circuit 17 and the controller 19 are attached to the housing 29 and disposed entirely within the sensor housing 29. In an embodiment, the sensor housing 29 is included in an access point to a location, for example at a door, gate, elevator, or the like. In an embodiment, the sensor housing 29 is included in a device to which access is controlled based on the detection of the one or more analytes by the sensor 5, for example, a mobile phone, a computer such as a workstation, industrial equipment, construction equipment, or any other suitable device to which access is controlled based on sensor 5.

The receive antenna 13 is decoupled or detuned with respect to the transmit antenna 11 such that electromagnetic coupling between the transmit antenna 11 and the receive antenna 13 is reduced. The decoupling of the transmit antenna 11 and the receive antenna 13 increases the portion of the signal(s) detected by the receive antenna 13 that is the response signal(s) 23 from the target 7, and minimizes direct receipt of the transmitted signal 21 by the receive antenna 13. The decoupling of the transmit antenna 11 and the receive antenna 13 results in transmission from the transmit antenna 11 to the receive antenna 13 having a reduced forward gain ($S_{21}$) and an increased reflection at output ($S_{22}$) compared to antenna systems having coupled transmit and receive antennas.

In an embodiment, coupling between the transmit antenna 11 and the receive antenna 13 is 95% or less. In another embodiment, coupling between the transmit antenna 11 and the receive antenna 13 is 90% or less. In another embodiment, coupling between the transmit antenna 11 and the receive antenna 13 is 85% or less. In another embodiment, coupling between the transmit antenna 11 and the receive antenna 13 is 75% or less.

Any technique for reducing coupling between the transmit antenna 11 and the receive antenna 13 can be used. For example, the decoupling between the transmit antenna 11 and the receive antenna 13 can be achieved by one or more intentionally fabricated configurations and/or arrangements between the transmit antenna 11 and the receive antenna 13 that is sufficient to decouple the transmit antenna 11 and the receive antenna 13 from one another.

For example, in one embodiment described further below, the decoupling of the transmit antenna 11 and the receive antenna 13 can be achieved by intentionally configuring the transmit antenna 11 and the receive antenna 13 to have different geometries from one another. Intentionally different geometries refers to different geometric configurations of the transmit and receive antennas 11, 13 that are intentional. Intentional differences in geometry are distinct from differences in geometry of transmit and receive antennas that may occur by accident or unintentionally, for example due to manufacturing errors or tolerances.

Another technique to achieve decoupling of the transmit antenna 11 and the receive antenna 13 is to provide appropriate spacing between each antenna 11, 13 that is sufficient to decouple the antennas 11, 13 and force a proportion of the electromagnetic lines of force of the transmitted signal 21 into the target 7 thereby minimizing or eliminating as much as possible direct receipt of electromagnetic energy by the receive antenna 13 directly from the transmit antenna 11 without traveling into the target 7. The appropriate spacing between each antenna 11, 13 can be determined based upon factors that include, but are not limited to, the output power of the signal from the transmit antenna 11, the size of the antennas 11, 13, the frequency or frequencies of the transmitted signal, and the presence of any shielding between the antennas. This technique helps to ensure that the response detected by the receive antenna 13 is measuring the analyte (s) 9 and is not just the transmitted signal 21 flowing directly from the transmit antenna 11 to the receive antenna 13. In some embodiments, the appropriate spacing between the antennas 11, 13 can be used together with the intentional difference in geometries of the antennas 11, 13 to achieve decoupling.

In one embodiment, the transmit signal (or each of the transmit signals) can be transmitted over a transmit time that is less than, equal to, or greater than about 300 ms. In another embodiment, the transmit time can be than, equal to, or greater than about 200 ms. In still another embodiment, the transmit time can be less than, equal to, or greater than about 30 ms. The transmit time could also have a magnitude that is measured in seconds, for example 1 second, 5 seconds, 10 seconds, or more. In an embodiment, the same transmit signal can be transmitted multiple times, and then the transmit time can be averaged. In another embodiment, the transmit signal (or each of the transmit signals) can be transmitted with a duty cycle that is less than or equal to about 50%.

Further information on the sensor 5 and its components and variations thereof can be found in U.S. Pat. Nos. 11,063,373, 11,234,619, 11,031,970, 11,223,383, 11,058,317, 11,058,331, 11,193,923, 10,548,503, 11,330,997, 11,033,208, 11,234,618, 11,284,819, and 11,284,820, the entire contents of which are incorporated herein by reference in their entirety.

FIG. 2 shows a flowchart of a method for access control according to an embodiment. Method 40 includes non-invasively detecting a presence or amount of one or more analytes 42. The non-invasive detection at 42 includes generating a transmit signal 44, transmitting the transmit signal into a target 46, receiving a response at 48, and processing the response 50. The method 40 further includes determining an identity and/or a status of the individual including the target at 52, determining access for the individual based on the identity and/or status at 54, and granting or denying the access to the individual at 56.

Non-invasive detection of one or more analytes is performed at 42. The non-invasive detection of the one or more analytes is at a target that is part of an individual seeking access according to method 40. The non-invasive detection at 42 can be performed using a sensor such as the sensor 5 described above and shown in FIG. 1. Detection of the one or more analytes at 42 can include generating a transmit signal 44. The transmit signal can be generated at 44 by a transmit circuit of a sensor, such as transmit circuit 15 of sensor 5 as described above and shown in FIG. 1. The detection of the one or more analytes at 42 can also include transmitting the transmit signal into the target 46. The transmit signal can be transmitted into the target by a transmit antenna of the sensor, such as transmit antenna 11 as described above and shown in FIG. 1. Detection of the one or more analytes at 42 can further include obtaining a response signal 48. The response signal results from the transmitting of the first transmit signal into the target. The first response signal can be obtained using a receive antenna of the sensor such as receive antenna 13 of sensor 5 as described above and shown in FIG. 1. The response obtained at 48 can be processed at 50 to determine a presence or amount of the one or more analytes, for example through converting the received response signal(s) to values indicative of a presence or amount of the one or more analytes.

An identity and/or status of the individual is determined 52 based on the presence or amount of the one or more analytes detected at 42. The identity of the individual can be an identification of the individual including the target as a particular individual, or determining whether the individual including the target is a part of a particular group. The identity can be determined, for example, by comparing the presence or amount of at least some of the one or more analytes to known analyte presences or levels associated with particular individuals or groups that the individual may belong to. The one or more analytes used to determine identity can be, for example, DNA sequences, proteins, hormones, bacteria, viruses, portions thereof, particular conformations thereof, combinations thereof, and/or ratios thereof, and the like. The detected presence or amounts of the one or more analytes can be compared to individual or group profiles including specific analytes, ranges and/or ratios for one or more particular analytes, conditional logic regarding combinations, ratios, or the like of the one or more analytes, or any other suitable information for determining whether an individual meets the profile based on the one or more analytes. The status of the individual can be any transient state that can be characterized by the detection of one or more analytes. Non-limiting examples of statuses of the individual that can be determined based on the one or more analytes at 52 can include a sobriety state, an intoxication state, an alert state, a tired state, certain emotional states such as stress or anger, sympathetic or parasympathetic nervous states, glucose states such as high or low blood sugar states, and the like. For example, a sobriety state or an intoxication state can be determined based on the presence or absence of recreational drugs, or amounts of such recreational drugs exceeding predetermined thresholds. Other states can be based on other suitable analytes such as prescription or over-the-counter drugs, metabolites, hormones, bacteria, viruses, glucose, or particular levels, combinations, or ratios thereof. For example, a communicable disease state can be based on a presence or absence of one or more pathogens of interest among the detected one or more analytes. The status of the individual can be determined by comparing at least some of the one or more analytes detected at 42 to criteria for one or more statuses to be determined. The criteria for the statuses can include the presence and/or amount of one or more analytes, conditional logic regarding combinations or ratios of a plurality of analytes, or any other suitable. In an embodiment, the status criteria can be particular to an individual. In an embodiment, the status criteria can be applied to any individual seeking access according to method 40. At 52, one or both of the identity of the individual and the status of the individual seeking access can be determined based on the one or more analytes detected at 42.

Access for the individual is determined at 54, based on one or both of the identity and the status of the individual. In an embodiment, the identity of the individual can be used to determine the access for the individual at 54. For example, when the identity of the individual matches an individual permitted access to the location or device, such as an owner of the location or device, an individual on a list of permitted persons such as employees, service providers, renters, guests, or the like, or when the individual is categorized as a member of a group granted access to a location or device. In an embodiment, the identity of the individual can be compared to a list of individuals or groups to be denied access, and access denied accordingly if the individual is a person or part of a group to be denied access. In an embodiment, the status of the individual can be used to determine access for the individual at 54. The access can be granted or denied based on the presence or absence of one or more statuses or combinations thereof determined at 52. For example, access to a location or device can be denied when intoxication is determined at 52, and access can be granted when sobriety is determined at 52 or when intoxication is not determined at 52. The access determination at 54 can be based on any status or combinations thereof, such as requiring both sobriety and alertness to be determined in order for access to be provided to a location or device. In an embodiment, both the identity and the status can be used in determining access for the individual at 54, for example, requiring both that the identity of the individual match that of a permitted access to the location or device while also requiring the presence or absence of one or more certain states in order for the access to be granted, with access denied to other individuals and/or when a person of the proper identity is in a state preventing the granting of access or lacking a state required for granting of access. In an embodiment, one or more additional factors can further be included in the determination of access at 54. For example, the date, time, current or predicted ambient conditions (for example, weather), and the like can further be used in a determination of access. For example, in addition to identity and/or status, access to a device can be conditioned on the access being sought within a permitted time of day, such as during working hours, being during daylight hours, being on particular dates, when a device is within a particular location, and the like. For example, an individual can be granted access during particular ranges of dates, such as periods of rental of a location or device. In an embodiment, current or predicted ambient conditions such as temperature, precipitation, and the like can be a further condition on which the access is determined, for example, blocking use of a device based on precipitation or temperature, even when the identity and/or status of the user would otherwise lead to a determination of access. In an embodiment, the access granted is access to an entire location or device, or the entire set of functionalities of the device. In an embodiment, the access granted can be partial access, such as access to particular sub-locations within a location, or access to only particular functionalities of the device. For example, different access levels having different identity and/or status criteria can be provided, corresponding to different levels of access to locations, devices, or functionalities thereof. The functionalities can be, for example, particular capabilities, applications and/or software, connections made by the device, combinations thereof, and the like. Specific device functionalities or sub-locations can have access conditioned on different identities and/or statuses from those allowed access to other functionalities or sub-locations. The different identities and/or statuses for access to particular functionalities or sub-locations can be, for example, set by users, device or location owners, or the like, for example based on characteristics of the sub-location or functionalities. For example, certain applications or device connections directed to executing financial transactions can be restricted to particular individuals and/or statuses that differ from the identities and/or statuses that can access other functionalities of the device. In another example, a specific sub-location such as a specific individual's office or a room containing an electrical panel of the location can have access criteria differing from other sub-locations within the location.

The determined access is granted or denied to the individual at 56. The granting or denial of access can be any suitable granting or denial of access based on the location or device to which access is controlled according to method 40. For example, when the access being controlled is access to a location, the granting or denial of access at 56 can include the locking or unlocking of a door or gate, calling an elevator or allowing the elevator to reach selected floors, or the like. When the access being controlled is access to a device, the granting or denial of access can include locking or unlocking the device or specific applications or functionalities thereof, starting or preventing starting of the device, performance of particular functionalities of the device, or the like. In an embodiment, granting or denying access to the individual at 56 can include providing or not providing access information to the individual. The access information can be, for example, a code such as an alphanumeric code for the individual to input at an access interface, a code or image such as a QR code to be scanned at an access interface, or the like. The access information can be provided to the individual, for example, at a mobile device of the individual.

FIG. 3 shows a system for access control for a location according to an embodiment. Location access control system 60 includes location access 62, access interface 64, and controller 66. Optionally, location access control system 60 can further include a mobile device 68 and/or a remote server 70.

Location access control 60 is configured to control access to a particular location. The location is a region of space that is sectioned off by walls, fences, gates, doors, and the like. In an embodiment, access to the location can be by way of an elevator. Access to the location can be controlled at one or more location accesses 62. Each location access 62 is an entry to the location that can be controlled to permit or deny access, such as lockable doors or gates, elevators to the location, or the like. An access interface 64 can be provided at the location access 62. The access interface 64 is an interface that obtains the identity and/or status of the individual seeking access at the location access 62, or an access permission thereof. In an embodiment, the access interface 64 includes a sensor such as the sensor 5 shown in FIG. 1 and described above. In such an embodiment, the access interface 64 detects the presence or amount of one or more analytes by the sensor. The presence or amount of the one or more analytes detected by the sensor at access interface 64 can then be processed, at a controller included in access interface 64, at mobile device 68 such as a wearable device, a smartphone, or the like, and/or remote server 70 to determine the identity and/or status of the individual seeking access. In an embodiment, the mobile device 68 can include the sensor such as sensor 5 to detect the presence or amount of the one or more analytes. The mobile device 68 can communicate the presence or amount of the one or more analytes to one or more of access interface 64 and/or remote server 70. The detection of the presence or amount of the one or more analytes can be processed to determine the identity and/or status of the individual at a controller included in access interface 64, at mobile device 68, and/or remote server 70. The access permission of the individual can be determined based on the identity and/or status, for example at a controller included in access interface 64, at mobile device 68, and/or remote server 70. The determinations of the identity and/or status and the access permission can be made separately or together at any one or more of the access interface 64, mobile device 68, and/or remote server 70. The access interface 64 and mobile device 68 and/or remote server 70 can be in communication with one another through any suitable wired or wireless communications, with non-limiting examples of communications including wired connections (direct or through one or more buses or other devices), Bluetooth, wireless data connections such a 4G, 5G, LTE or the like, or Wi-Fi. The access permission can optionally further be based on additional external factors additional to identity and/or status, such as time, date, event-based triggers, or the like. The location access 62 can be controlled according to the access permission to permit or deny access to the location to the individual. For example, location access 62 can be controlled according to the access permission by locking, unlocking, or maintaining a locked or unlocked state of a gate or door, allowing or denying elevator access to the location such as controlling the floors an elevator can travel to, or the like.

FIG. 4 shows a system for access control for a device according to an embodiment. The device access control system 75 includes the device 77. The device access control system can optionally further include one or more of a mobile device 79, a remote server 81, and/or a sensor unit 83.

Device 77 can be any suitable device for which access to at least some functionalities is to be controlled. Device 77 can include, but are not limited to, computing devices such as mobile devices such as smartphones, tablets, computers such as laptop computers, desktop computers, gaming devices such as electronic slot machines, electric gaming tables, and the like, industrial or construction machinery, commercial devices such as sales terminals or inventory management terminals, vehicles, and the like. In an embodiment, the device 77 includes a sensor such as sensor 5 to detect the presence or amount of one or more analytes in a potential user. In an embodiment, a discrete sensor unit 83 separate from the device 77 can be provided to detect the presence or amount of the one or more analytes. The sensor unit 83 can include a sensor such as sensor 5. In an embodiment, the sensor can be included in a mobile device 79, such as a wearable device, a smartphone, or the like. The sensor, whether included in device 77, mobile device 79, or provided as a discrete sensor unit 83 can transmit a transmit signal into a target included in the individual seeking access to the device. A response is obtained, and the response processed to detect a presence or amount of the one or more analytes. The processing of the response can be at any suitable processor, such as a controller included in the device 77, sensor unit 83, mobile device 79, or at a remote server 81. From the presence or amount of the one or more analytes, an identity and/or status of the individual seeking access to device 77 can be determined. The determination of identity and/or status can be at any one or more of a controller included in the device 77, sensor unit 83, mobile device 79, or at a remote server 81. An access permission can be determined based on the identity and/or status. The access permission can be determined at any one or more of a controller included in the device 77, sensor unit 83, mobile device 79, or at a remote server 81. The device 77, sensor unit 83, mobile device 79, and/or remote server 81, when included in access control system 75, can be in communication with one another through any suitable wired or wireless communications, with non-limiting examples of communications including wired connections (direct or through one or more buses or other devices), Bluetooth, wireless data connections such a 4G, 5G, LTE or the like, or Wi-Fi. The access permission can include access to the device 77 generally, or access to one or more particular functionalities of the device 77. The particular functionalities can include, for example, one or more software applications, access to one or more subsets of functionalities of the device, and the like. For example, access permissions for device 77 when device 77 is a computing device such as a smartphone or a personal computer can include requiring confirmation of identity and/or status of the user to allow financial transactions to be made, limits on contacts that can be messaged based on identity and/or status of the user, and the like. Particular functionalities of other devices 77 such as industrial or construction equipment and the like can likewise be controlled based on identity and/or status of the user, for example, allowing access to different functionalities for different sets or classifications of individuals and/or the particular statuses thereof. In embodiments, the access to the device can be access to the device using a profile or account of the individual for whom identity and optionally status are determined for based on the one or more analytes, for example using a specific user account on a computer device, a player account on gaming device, or the like.

The examples disclosed in this application are to be considered in all respects as illustrative and not limitative. The scope of the invention is indicated by the appended claims rather than by the foregoing description; and all changes which come within the meaning and range of equivalency of the claims are intended to be embraced therein.

The invention claimed is:

1. An access control system, comprising:
   a sensor comprising:
      an antenna array having at least one transmit antenna and at least one receive antenna, the at least one transmit antenna is positioned and arranged to transmit a transmit signal into a human target, and the at least one receive antenna is positioned and arranged to detect a response resulting from transmission of the transmit signal by the at least one transmit antenna into the human target;
a transmit circuit that is electrically connectable to the at least one transmit antenna, the transmit circuit is configured to generate a transmit signal to be transmitted by the at least one transmit antenna, the transmit signal is in a radio or microwave frequency range of the electromagnetic spectrum; and
a receive circuit that is electrically connectable to the at least one receive antenna, the receive circuit is configured to receive a response detected by the at least one receive antenna,
a controller configured to:
determine an identity and/or status of the human target, based on a presence or amount of one or more analytes determined by processing of the response; and
provide or deny access to the human target based on the identity and/or status of the individual seeking access, wherein the access is access to a device.

2. The access control system of claim 1, wherein the controller is configured to process the response to determine the presence or amount of the one or more analytes.

3. The access control system of claim 1, wherein the controller is configured to provide or deny access to the individual based on the status of the human target.

4. The access control system of claim 3, wherein the status of the human target includes an intoxication state of the individual seeking access.

5. The access control system of claim 1, wherein the sensor is included in the device.

6. An access control system, comprising:
a sensor comprising:
an antenna array having at least one transmit antenna and at least one receive antenna, the at least one transmit antenna is positioned and arranged to transmit a transmit signal into a human target, and the at least one receive antenna is positioned and arranged to detect a response resulting from transmission of the transmit signal by the at least one transmit antenna into the human target;
a transmit circuit that is electrically connectable to the at least one transmit antenna, the transmit circuit is configured to generate a transmit signal to be transmitted by the at least one transmit antenna, the transmit signal is in a radio or microwave frequency range of the electromagnetic spectrum; and
a receive circuit that is electrically connectable to the at least one receive antenna, the receive circuit is configured to receive a response detected by the at least one receive antenna,
a controller configured to:
determine an identity and/or status of the human target, based on a presence or amount of one or more analytes determined by processing of the response; and
provide or deny access to the human target based on the identity and/or status of the individual seeking access, wherein the access is access to one or more functionalities of a device.

7. The access control system of claim 6, wherein the sensor is included in the device.

8. A method of controlling access, comprising:
non-invasively detecting one or more analytes, wherein non-invasively detecting the one or more analytes includes:
generating a transmit signal using a transmit circuit of a sensor;
transmitting the transmit signal into a human target using a transmit antenna of the sensor, the transmit signal in a radio or microwave frequency range of the electromagnetic spectrum;
detecting a response resulting from transmitting the transmit signal into the human target using a receive antenna of the sensor; and
processing the response to determine a presence or amount of the one or more analytes in the human target;
determining, based on the presence or amount of the one or more analytes in the human target, an identity and/or status of the human target at a controller; and
allowing or denying access to the human target based on the identity and/or status of the individual seeking access, wherein the access is to a device.

9. The method of claim 8, wherein the controller is configured to provide or deny access to the individual based on the status of the human target.

10. The method of claim 9, wherein the status of the individual seeking access includes an intoxication state of the human target.

11. A method of controlling access, comprising:
non-invasively detecting one or more analytes, wherein non-invasively detecting the one or more analytes includes:
generating a transmit signal using a transmit circuit of a sensor;
transmitting the transmit signal into a human target using a transmit antenna of the sensor, the transmit signal in a radio or microwave frequency range of the electromagnetic spectrum;
detecting a response resulting from transmitting the transmit signal into the human target using a receive antenna of the sensor; and
processing the response to determine a presence or amount of the one or more analytes in the human target;
determining, based on the presence or amount of the one or more analytes in the human target, an identity and/or status of the human target at a controller; and
allowing or denying access to the human target based on the identity and/or status of the individual seeking access, wherein the access is to one or more functionalities of a device.

12. A method of access control, comprising:
confirming a biological identity of an individual using a non-invasive sensor by transmitting, using at least one transmit antenna, first transmit signals in a radio or microwave frequency range of the electromagnetic spectrum into the individual and detecting responses resulting from transmitting the first transmit signals into the individual using at least one receive antenna;
determining a presence and/or amount of an analyte in the individual using a non-invasive sensor by transmitting, using at least one transmit antenna, second transmit signals in a radio or microwave frequency range of the electromagnetic spectrum into the individual and detecting responses resulting from transmitting the second transmit signals into the individual using at least one receive antenna;

permitting or blocking access based on the confirming and the determining.

13. The method of claim 12, wherein the non-invasive sensor used in the confirming is the same non-invasive sensor used in the determining.

14. The method of claim 12, wherein the non-invasive sensor used in the confirming is different from the non-invasive sensor used in the determining.

* * * * *